(12) United States Patent
Gordon et al.

(10) Patent No.: US 9,303,125 B2
(45) Date of Patent: Apr. 5, 2016

(54) METHOD OF FORMING PARTICLES FROM AN OIL-IN-WATER EMULSION

(71) Applicant: Dow Corning Corporation, Midland, MI (US)

(72) Inventors: Glenn Viaplana Gordon, Midland, MI (US); Donald Taylor Liles, Midland, MI (US)

(73) Assignee: Dow Corning Corporation, Midland, MI (US)

(*) Notice: Subject to any disclaimer, the term of this patent is extended or adjusted under 35 U.S.C. 154(b) by 0 days.

(21) Appl. No.: 14/382,011

(22) PCT Filed: Mar. 1, 2013

(86) PCT No.: PCT/US2013/028548
§ 371 (c)(1),
(2) Date: Aug. 29, 2014

(87) PCT Pub. No.: WO2013/130938
PCT Pub. Date: Sep. 6, 2013

(65) Prior Publication Data
US 2015/0031825 A1      Jan. 29, 2015

Related U.S. Application Data

(60) Provisional application No. 61/605,277, filed on Mar. 1, 2012.

(51) Int. Cl.
| | | |
|---|---|---|
| *C08G 77/452* | (2006.01) | |
| *C08G 77/16* | (2006.01) | |
| *C08G 77/26* | (2006.01) | |
| *C08G 77/388* | (2006.01) | |
| *C08G 77/458* | (2006.01) | |

(Continued)

(52) U.S. Cl.
CPC ............. *C08G 77/452* (2013.01); *A61K 8/898* (2013.01); *A61Q 19/00* (2013.01); *C08G 77/16* (2013.01); *C08G 77/26* (2013.01); *C08G 77/388* (2013.01); *C08G 77/458* (2013.01); *A61K 2800/10* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 4,186,104 A | * | 1/1980 | Pirson ............... | B01D 19/0409 516/123 |
| 5,013,577 A | * | 5/1991 | Wright ............... | C07F 7/10 427/503 |

(Continued)

FOREIGN PATENT DOCUMENTS

JP            2000-026702         1/2000

OTHER PUBLICATIONS

Oct. 16, 2015, First Office Action of Chinese patent application No. 201380011665.6; Method of Forming Particles from an Oil-in-water Emulsion; Dow Coming Corporation (original and translation).

*Primary Examiner* — Robert S Loewe
(74) *Attorney, Agent, or Firm* — Baltazar Gomez

(57) ABSTRACT

Particles having an average diameter of at least 30 nanometers include a polymerization product of a silanol, a cyclic silazane, and an isocyanate. The particles are formed in an oil-in-water emulsion which includes less than 0.1 weight percent of a hydrophobic costabilizer. The particles are formed by a method including the step of reacting the silanol and the cyclic silazane and the isocyanate and the step of forming the oil-in-water emulsion.

19 Claims, 3 Drawing Sheets

(51) Int. Cl.
*A61K 8/898* (2006.01)
*A61Q 19/00* (2006.01)

(56) References Cited

U.S. PATENT DOCUMENTS

| | | | | |
|---|---|---|---|---|
| 5,643,581 A | * | 7/1997 | Mougin | A61K 8/898 424/401 |
| 5,852,110 A | * | 12/1998 | Gee | C08G 77/26 524/714 |
| 6,235,834 B1 | | 5/2001 | Gee et al. | |
| 6,326,013 B1 | * | 12/2001 | Lemann | A61K 8/06 424/401 |
| 7,026,424 B2 | | 4/2006 | Schafer et al. | |
| 7,491,786 B2 | * | 2/2009 | Scheim | C08G 77/26 528/38 |
| 7,823,633 B2 | | 11/2010 | Hartwell | |
| 8,877,167 B2 | | 11/2014 | Schultze et al. | |
| 9,029,428 B2 | | 5/2015 | Kojima et al. | |
| 2002/0049296 A1 | * | 4/2002 | Schafer | C07F 7/0874 528/10 |
| 2003/0176613 A1 | * | 9/2003 | Hohberg | C08G 18/0823 528/28 |
| 2004/0236056 A1 | * | 11/2004 | Schindler | C08L 83/14 528/38 |
| 2004/0254325 A1 | * | 12/2004 | Kuepfer | C08G 18/289 528/25 |
| 2006/0111452 A1 | | 5/2006 | Wallace et al. | |
| 2006/0205861 A1 | * | 9/2006 | Gordon | C08L 83/08 524/506 |
| 2007/0106045 A1 | | 5/2007 | Lange et al. | |
| 2007/0112129 A1 | | 5/2007 | Licht et al. | |
| 2008/0127429 A1 | * | 6/2008 | Brun | A61K 8/31 8/435 |
| 2008/0171010 A1 | * | 7/2008 | Brun | A61Q 5/12 424/70.12 |
| 2009/0143496 A1 | * | 6/2009 | Ziche | C07C 265/14 522/148 |
| 2012/0064018 A1 | * | 3/2012 | Schultze | A61K 8/898 424/59 |
| 2013/0189521 A1 | * | 7/2013 | Fukuju | C01B 33/16 428/402 |

\* cited by examiner

METHOD OF FORMING PARTICLES FROM AN OIL-IN-WATER EMULSION

RELATED APPLICATIONS

This application is the National Stage of International Patent Application No. PCT/US2013/028548, filed on Mar. 1, 2013, which claims priority to and all the advantages of U.S. Provisional Patent Application No. 61/605,277, filed on Mar. 1, 2012, the contents of which are incorporated herein by reference in their entirety.

FIELD OF THE DISCLOSURE

The present disclosure generally relates to a method of forming particles in an oil-in-water emulsion that is substantially free of a hydrophobic costabilizer. More specifically, the particles have a particular diameter and are formed from reacting a silanol, a cyclic silazane, and an isocyanate. The present disclosure also relates to the oil-in-water emulsion itself.

DESCRIPTION OF THE RELATED ART

Emulsions and particles dispersed within emulsions are known to be useful in plastics, coatings, and cosmetics and can be formed using production processes known in the art. One type of process forms a "miniemulsion." As is well recognized in the art, miniemulsions include particles having sizes of less than 500 nanometers and include hydrophobic costabilizers. The terminology "hydrophobic costabilizer" is also well known in the art and refers to highly water insoluble compounds that are added to the miniemulsions to increase stability of the particles against collisional degradation and diffusional degradation (e.g. Ostwald ripening). The hydrophobic costabilizers also increase a swelling capacity of the particles which distinguishes miniemulsions from conventional emulsions having particle sizes of greater than 500 nanometers. The hydrophobic costabilizers used in miniemulsions are hydrocarbons, such as hexadecane, halogenated hydrocarbons, and hydrophobic oils and must be sufficiently hydrophobic to increase the stability and swelling capacity of the particles. However, use of hydrophobic costabilizers to form miniemulsions is expensive due to raw material costs and adds additional production steps and time to commercial formation of emulsions and particles dispersed therein. More specifically, additional time and money must be spent in the commercial processes used to form the miniemulsions. In addition, the halogenated hydrocarbons used in miniemulsions are not environmentally friendly.

Another type of process forms particles in an emulsion at an "oil-water" interface but kinetically favors formation of small particles (diameters less than 500 nm) with large surface areas. This renders production of larger particles difficult and energy consuming. This process also typically requires long batch times and caustic materials, which must be neutralized. These requirements increase production costs which are typically passed along to the end user.

Accordingly, there remains an opportunity to form improved emulsions and particles formed therein. There also remains an opportunity to develop an improved method of forming such particles both economically and efficiently. There further remains an opportunity to include these particles in a variety of products to improve physical and chemical characteristics of the products.

SUMMARY OF THE DISCLOSURE AND ADVANTAGES

The instant disclosure provides an oil-in-water emulsion including less than 0.1 weight percent of a hydrophobic costabilizer and also including particles having an average diameter of at least 30 nanometers. The particles include a polymerization product of a silanol, a cyclic silazane, and an isocyanate. The particles are formed from a method including the step of forming an oil-in-water (o/w) emulsion. The instant disclosure also provides a personal care composition that includes the particles formed from the method of this disclosure.

The instant disclosure provides an efficient and cost-effective method for forming particles in the oil-in-water emulsion with a minimal amount of a hydrophobic costabilizer. Minimizing the amount of the hydrophobic costabilizer decreases production costs and times needed to form the particles. In addition, the oil-in-water emulsion allows the particles to be handled easily and allows for quality checks on the particles to be performed efficiently and accurately. The oil-in-water emulsion also allows for a variety of compounds to be utilized to form particles having customized physical and chemical properties. Further, the oil-in-water emulsion allows highly viscous particles to be formed and transported with greater ease. Even further, manipulation of the amount of the isocyanate used in this disclosure allows for simple control of a number average molecular weight of the particles thereby promoting customization and efficient use of the particles.

BRIEF DESCRIPTION OF THE SEVERAL VIEWS OF THE DRAWINGS

Other advantages of the present disclosure will be readily appreciated, as the same becomes better understood by reference to the following detailed description when considered in connection with the accompanying drawings wherein.

DETAILED DESCRIPTION OF THE DISCLOSURE

Figure 1:
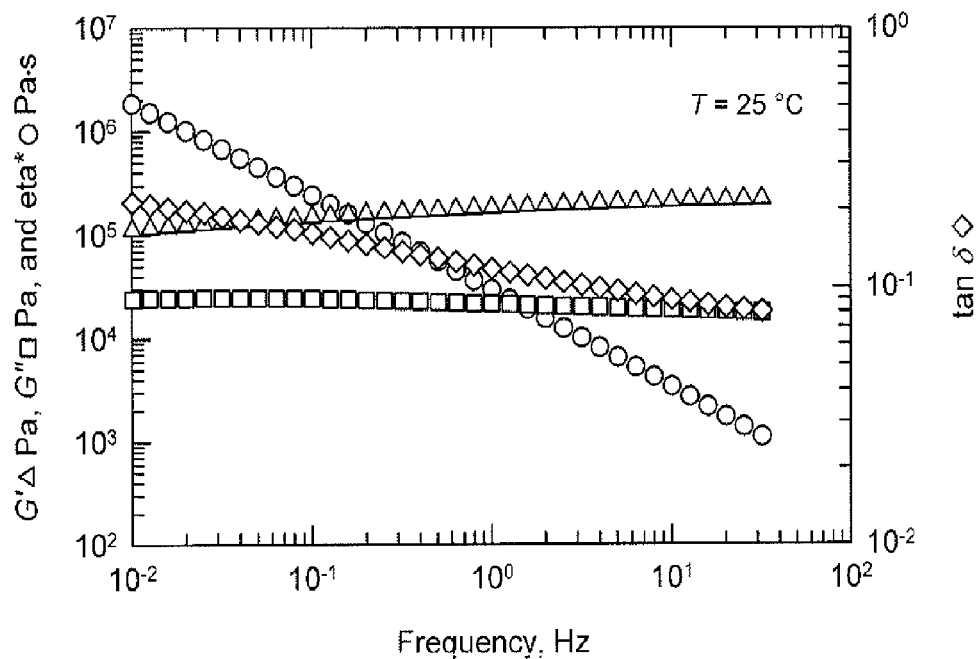
FIG. 1 is a dynamic mechanical analysis/rheological profile of the polymer of Example 1.

The instant disclosure provides a method of forming particles. It is to be understood that the terminology "particles" may refer to a single particle or a plurality of particles. Thus, the terminology "particle" and "particles" are used interchangeably herein. The particles have an average diameter (i.e., mean particle size) of at least 30 nanometers (nm). In one embodiment, the particles have an average diameter of at least 100 nm. In another embodiments, the particles have an average diameter of from 200 to 500 nm, 200 to 900, 200 to 800, 200 to 700, 200 to 600, 200 to 400, 200 to 300, 500 to 900, 600 to 800, 700 to 800, 600 to 900, 700 to 900, nm, etc. In still another embodiment, the particles have an average diameter of greater than 500 nm. In yet another embodiment, the particles have an average diameter of from greater than 500 to 1,000 nm, i.e., greater than 500 and up to 1,000 nm. In other embodiments, the particles typically have an average diameter of greater than 500, more typically of from 500 to 2,500, still more typically of from 500 to 1,500, and most typically of from 500 to 1,000, nm. In still other embodiments, the particles have an average diameter of from 1-50 microns, of from 1 to 5, of from 1 to 10, of from 5 to 10, of from 5 to 50, of from 10 to 45, of from 15 to 40, of from 20 to 35, or of from 25 to 30, microns. The average diameter of the particles is typically determined by light scattering using a Nanotrac® particle size analyzer.

The particles of this disclosure are formed in an oil-in-water (o/w) emulsion. As is known in the art, o/w emulsions typically include a non-polar dispersed phase (e.g. oil) in an aqueous continuous phase (e.g. water). The o/w emulsion of this disclosure is typically a liquid while the particles themselves may be solids, liquids, gasses, or combinations thereof and may be dispersed in one or more of the same. The particles are usually liquids or solids that are immiscible with, and dispersed in, the continuous phase. The particles may include liquids as diluents, such that no external or additional liquids are added to the o/w emulsion. Alternatively, the o/w emulsion may include a liquid independent of any diluent.

As is well recognized in the art, the terminology "oil" of the o/w emulsion may include any non-polar substance (e.g. liquid) that is substantially immiscible with water or any other polar substance, as appreciated in the art. Typically, the "oil" is a non-polar compound and may be a liquid, gum, paste, etc. In one embodiment, the "oil" of this disclosure includes a silanol, a cyclic silazane, an amino-functional polysiloxane, and/or an isocyanate, reaction or polymerization products thereof, or combinations thereof. Each of the silanol, the cyclic silazane, the amino-functional polysiloxane, and the isocyanate are described in greater detail below. Typically, the "oil" is present in an amount of from 5 to 95, more typically of from 30 to 80, and most typically of from 50 to 70, parts by weight per 100 parts by weight of the o/w emulsion.

The terminology water of the o/w emulsion may include molecular water ($H_2O$) such as tap water, well water, purified water, deionized water, and combinations thereof. In one embodiment, the water of the o/w emulsion consists essentially of molecular water and does not include any other diluents such as organic compounds, acids, etc. In another embodiment, the water of the o/w emulsion consists of molecular water, such as purified water. Of course, it is to be understood that the purified water may still contain trace impurities. Typically, the water is present in an amount of from 5 to 95, more typically of from 20 to 80, and most typically of from 30 to 50, parts by weight per 100 parts by weight of the o/w emulsion.

In one embodiment, the o/w emulsion includes a polar substance (e.g. a liquid) that is substantially miscible with the water, as appreciated in the art. The polar substance may be a polar organic compound, such as an alcohol, acid, or the like, a surfactant, or combinations thereof. In other embodiments, the o/w emulsion includes a first surfactant and a second surfactant or multiple surfactants. The surfactant may be combined with the "oil" or the water of the o/w emulsion. Typically, the surfactant is combined with the water of the o/w emulsion. Surfactants are also known as emulsifiers, emulgents, and tensides. Relative to this disclosure, the terminology "surfactant", "emulsifier", "emulgent", and "tenside" may be used interchangeably. Surfactants reduce a surface tension of a liquid by adsorbing at a liquid-gas interface. Surfactants also reduce interfacial tension between polar and non-polar molecules by adsorbing at a liquid-liquid interface. Without intending to be bound by any particular theory, it is believed that surfactants act at these interfaces and are dependent on various forces including, excluded volume repulsion forces, electrostatic interaction forces, van der waals forces, entropic forces, and steric forces. In the instant disclosure, the surfactant may be chosen or manipulated based on one or more of these forces.

The surfactant, first and second surfactants, or first/second/and multiple surfactants may independently be selected from the group of non-ionic surfactants, cationic surfactants, anionic surfactants, amphoteric surfactants, and combinations thereof. Suitable non-ionic surfactants include, but are not limited to, alkylphenol alkoxylates, ethoxylated and propoxylated fatty alcohols, alkyl polyglucosides and hydroxyalkyl polyglucosides, sorbitan derivatives, N-alkylglucamides, alkylene oxide block copolymers such as block copolymers of ethylene oxide, propylene oxide and/or butylene oxide, polyhydroxy and polyalkoxy fatty acid derivatives, amine oxides, silicone polyethers, various polymeric surfactants based on polysaccharides, polymeric surfactants based on polyvinyl alcohol and polyacrylamide, and combinations thereof.

Suitable cationic surfactants include, but are not limited to, interface-active compounds including ammonium groups such as alkyldimethylammonium halides and compounds having the chemical formula $RR'R''R'''N^+X^-$ wherein R, R', R'', and R''' are independently selected from the group of alkyl groups, aryl groups, alkylalkoxy groups, arylalkoxy groups, hydroxyalkyl(alkoxy) groups, and hydroxyaryl(alkoxy) groups and wherein X is an anion.

Suitable anionic surfactants include, but are not limited to, fatty alcohol sulfates and sulfates of ethoxylated fatty alcohols. Further non-limiting examples of suitable anionic surfactants include alkanesulfonates, linear alkylbenzenesulfonates, linear alkyltoluenesulfonates, diphenyl sulfonates, and diphenylether sulfonates. Still further, the anionic surfactant may include olefinsulfonates and di-sulfonates, mixtures of alkene- and hydroxyalkane-sulfonates or di-sulfonates, alkyl ester sulfonates, sulfonated polycarboxylic acids, alkyl glyceryl sulfonates, fatty acid glycerol ester sulfonates, alkylphenol polyglycol ether sulfates, paraffinsulfonates, alkyl phosphates, acyl isothionates, acyl taurates, acyl methyl taurates, alkylsuccinic acids, alkenylsuccinic acids and corresponding esters and amides thereof, alkylsulfosuccinic acids and corresponding amides, mono- and di-esters of sulfosuccinic acids, acyl sarcosinates, sulfated alkyl polyglucosides, alkyl polyglycol carboxylates, hydroxyalkyl sarcosinates, and combinations thereof. Still further, polymeric anionic surfactants based on acrylic acid or sulfonated polystyrene, and combinations thereof, may also be used. Suitable ampholytic surfactants include, but are not limited to, aliphatic derivatives of secondary and/or tertiary amines which include an anionic group, betaine derivatives, and combinations thereof.

Additionally, the surfactant and/or first and second surfactants may independently include aliphatic and/or aromatic alkoxylated alcohols, LAS (linear alkyl benzene sulfonates), paraffin sulfonates, FAS (fatty alcohol sulfates), FAES (fatty alcohol ethersulfates), alkylene glycols, trimethylolpropane ethoxylates, glycerol ethoxylates, pentaerythritol ethoxylates, alkoxylates of bisphenol A, and alkoxylates of 4-methylhexanol and 5-methyl-2-propylheptanol, and combinations thereof. Further, the surfactant and/or first and second surfactants may include alkylpolysaccharides including linear or branched alkyl groups, linear or branched alkenyl groups, alkylphenyl groups, alkylene groups, and/or combinations thereof. Typically, the surfactant is present in an amount of from 0.1 to 100, more typically of from 0.01 to 5, even more typically of from 0.5 to 5, and most typically of from 1.5 to 2.5, parts by weight per 100 parts by weight of the oil phase in the o/w emulsion.

The o/w emulsion may also include a thickener. As is known in the art, thickeners increase a viscosity of the o/w emulsion at low shear rates while maintaining flow properties of the o/w emulsion at higher shear rates. Suitable thickeners for use in the Instant disclosure include, but are not limited to, polyalkylene oxides such as polyethylene oxide, polypropylene oxide, polybutylene oxide, and combinations thereof. In one embodiment, the thickener is selected from the group of algenic acid and its derivatives, polyethylene oxide, polyvinyl alcohol, methyl cellulose, hydroxypropylmethyl cellulose, alkyl and hydroxyalkyl cellulose, carboxymethyl cellulose, hydroxyethyl cellulose, guar gum, gum arabic, gum ghatic, polyvinylpyrrolidone, starch, modified starch, tamarind gum, xanthan gum, polyacrylamide, polyacrylic acid, and combinations thereof.

The thickener may be combined with the water or the "oil" before the o/w emulsion is formed. Typically, the thickener is combined with the water before the o/w emulsion is formed. Alternatively, the thickener may be combined with a liquid in which it is not soluble to form a mixture. This mixture may then be combined with the o/w emulsion after it has been formed. Examples of such liquids include, but are not limited to, propylene glycol, ethylene glycol, glycerin, and combinations thereof. In various embodiments, the thickener is typically present in an amount of from 0.001 to 25, more typically of from 0.05 to 5, and most typically of from 0.1 to 0.5, parts by weight per 100 parts by weight of the o/w emulsion.

The o/w emulsion may also include additives. The additives may include, but are not limited to, conductivity-enhancing additives, salts, dyes, perfumes, preservatives, plasticizers, active ingredients, colorants, labeling agents, rust inhibitors, anti-microbial compounds, and combinations thereof. In one embodiment, the conductivity-enhancing additive includes an ionic compound. In another embodiment, the conductivity-enhancing additives are generally selected from the group of amines, organic salts and inorganic salts, and mixtures thereof. Typical conductivity-enhancing additives include amines, quaternary ammonium salts, quaternary phosphonium salts, ternary sulfonium salts, and mixtures of inorganic salts with organic ligands. The additive may be present in either a continuous or a dispersed phase of the o/w emulsion in any amount selected by one of skill in the art. In various embodiments, the additive is typically present in amounts of from about 0.0001 to about 25%, more typically from about 0.001 to about 10%, and more typically from about 0.01 to about 1% based on the total weight of the particles.

The o/w emulsion of this disclosure is substantially free of a hydrophobic costabilizer. Minimizing the amount of the hydrophobic costabilizer decreases production costs and times needed to form the particles. The o/w emulsion typically includes less than 5, 4, 3, 2, 1, 0.1, 0.05, 0.01, 0.001, or 0.0001 weight percent of the hydrophobic costabilizer. In various embodiments, the hydrophobic costabilizer is present in the o/w emulsion in less than 900 and more typically of less than 100, parts, per one million parts of the o/w emulsion. Alternatively, the o/w emulsion may be completely free of the hydrophobic costabilizer. As is well known in the art, the terminology "hydrophobic costabilizer" refers to a highly water insoluble compound that increases the stability of emulsions against collisional degradation and diffusional degradation (e.g. Ostwald ripening) but that does not react with compounds used to form the particles of this disclosure. That is, the silanol, cyclic silazane, amino-functional polysiloxane, and isocyanate of the instant disclosure are not hydrophobic costabilizers and are specifically differentiated therefrom. The hydrophobic costabilizer typically includes hydrocarbons, such as hexadecane, halogenated hydrocarbons, hydrophobic oils such as olive oil, and combinations thereof. The hydrophobic costabilizers typically have a water solubility of less than $10^{-5}$, more typically of less than $10^{-6}$, and most typically of less than $10^{-7}$, g/liter water at 21° C., 1 bar.

The o/w emulsion of this disclosure may also be substantially free (i.e., including less than 5, 4, 3, 2, 1, 0.1, 0.05, 0.01, 0.001, or 0.0001, weight percent based on a total weight of the emulsion) of octamethylcyclotetrasiloxane and/or decamethylcyclopentasiloxane, which are common precursors used to make siloxanes. It is possible to form the o/w emulsion without, or with a minimized amount of, octamethylcyclotetrasiloxane and decamethylcyclopentasiloxane to increase the safety of the o/w emulsion and to increase the applicability of using the o/w emulsion in personal care products. Accordingly, the o/w emulsion may include less than 0.1, more typically less than 0.05, still more typically of less than 0.01, and most typically of less than 0.001, weight percent of the octamethylcyclotetrasiloxane and/or decamethylcyclopentasiloxane, based on a total weight of the emulsion. In this disclosure, the octamethylcyclotetrasiloxane and/or decamethylcyclopentasiloxane may be stripped before the silanol reacts with the cyclic silazane.

As is also known in the art, o/w emulsions typically have two different types of viscosities, a total viscosity and a viscosity of the dispersed phase, i.e., a viscosity of compounds within particles of this disclosure. The o/w emulsion of this disclosure typically has a total viscosity of at least 20 centistokes at a temperature of 25° C. using a Brookfield rotating disc viscometer equipped with a thermal cell and an SC4-31 spindle operated at a constant temperature of 25° C. and a rotational speed of 5 rpm. In various embodiments, the o/w emulsion has a total viscosity of at least 20 centistokes, more typically from about 30 to about 100 centistokes, most typically from about 40 to about 75 centistokes at a temperature of 25° C. using a Brookfield rotating disc viscometer equipped with a thermal cell and an SC4-31 spindle operated at a constant temperature of 25° C. and a rotational speed of 5 rpm.

The viscosity of the dispersed phase, i.e., the particles, is not limited and is not believed to affect the total viscosity of the o/w emulsion. In one embodiment, the particles are solid and have an infinite viscosity. In another embodiment, the particles have a dynamic viscosity of less than 100 million centipoise (cP) measured at a temperature of 25° C. and at $10^{-1}$ Hertz (Hz) using a controlled strain rheometer. In an alternative embodiment, the particles have a dynamic viscosity of greater than 100 million centipoise (cP) measured at a temperature of 25° C. and at $10^{-1}$ Hertz (Hz) using dynamic mechanical analysis (DMA) and an oscillatory rheometer equipped with parallel plates. In other embodiments, the particles typically have a dynamic viscosity of from $10^4$ to $10^{11}$, more typically of from $10^5$ to $10^{11}$, and still more typically of from $10^7$ to $10^{11}$, centipoise (cP), measured at a temperature of 25° C. using dynamic mechanical analysis (DMA) and an oscillatory rheometer equipped with parallel plates. However, the particles can have a dynamic viscosity outside of this range if desired.

In one embodiment, the particles include the polymerization product of the silanol, the cyclic silazane, and the isocyanate which are reacted in the o/w emulsion. In another embodiment, the particles include the polymerization product of the amino-functional polysiloxane and the isocyanate which are also reacted in the o/w emulsion. In this embodiment, the amino-functional polysiloxane typically comprises the reaction product of the silanol and the cyclic silazane. The reactions of the silanol, the cyclic silazane, the amino-functional polysiloxane, and the isocyanate are described in greater detail below.

Referring now to the silanol, it is well known in the art that the terminology "silanol" refers to compounds that have hydroxyl (—OH) groups bonded directly to one or more silicon atoms. The silanol of this disclosure may be any known in the art and may have one, two, or more than two hydroxyl groups bonded to one or more silicon atoms. In addition, the silanol may be a fluid, paste, resin, or gum. In one embodiment, the silanol has the chemical formula $H(OSiR^1R^2)_n OH$. In this formula, $R^1$ and $R^2$ may be independently selected from the group of alkyl groups, cyclic alkyl groups, aromatic groups, and combinations thereof. Typically, $R^1$ and $R^2$ are both methyl groups. In addition, "n" may be any number. Typically n is a number of from 1 to 10,000, 10 to 10,000, 1 to 2,000, or of from 10 to 2,000. Alternatively, n may be 1, 2, 3, 4, 5, 6, 7, 8, 9, or 10, or a number of from 100 to 1,500, from 100 to 1,000, from 200 to 800, or from 700 to 900. In one embodiment, n is approximately 800. In one embodiment, the silanol is further defined as a SiOH functional terminated polydiorganopolysiloxane.

Referring now to the cyclic silazane, it is well known in the art that the terminology "cyclic silazane" refers to cyclic compounds that include hydrides of silicon and nitrogen having straight or branched chains of silicon and nitrogen atoms joined by covalent bonds. The cyclic silazane of the instant disclosure may have the following chemical formula:

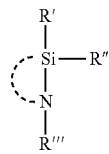

wherein the dashed line represents a cyclic structure having from 2 to 20 carbon atoms and R', R'', and R''' are each independently selected from the group of hydrogen atoms, aromatic groups, linear alkyl groups, branched alkyl groups, cyclic alkyl groups, and combinations thereof. In one embodiment, R' and R'' are both independently alkyl groups that may be the same or different and may be linear, branched, or cyclic and R''' is a hydrogen atom or an alkyl group having from 2 to 20 carbon atoms.

In further embodiments, the cyclic silazane has the following chemical formula:

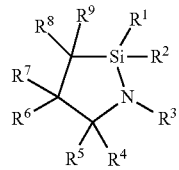

wherein each of $R^1$-$R^9$ is independently selected from the group of hydrogen atoms, aromatic groups, linear alkyl groups, branched alkyl groups, cyclic alkyl groups, and combinations thereof. In one embodiment, the cyclic silazane is further defined as 1,1,2,4-tetramethyl-1-sila-2-azacyclopentane (chemical formula: $C_7H_{17}NSi$), the chemical structure of which is set forth below:

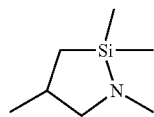

1,1,2,4-tetramethyl-1-sila-2-azacyclopentane

Referring now to the amino-functional polysiloxane, the amino-functional polysiloxane typically includes a polysiloxane backbone and an amino group bonded to the polysiloxane backbone. The amino-functional polysiloxane may include one amino group or more than one amino group bonded to the polysiloxane backbone. In addition, the amino group may be bonded anywhere within the polysiloxane backbone and is not limited to being bonded to any particular terminal or pendant group. In one embodiment, the amino group is a terminal group. Typically, the amino-functional polysiloxane is further defined as an amino-terminated polysiloxane having a polysiloxane backbone and one or two amino groups bonded to the polysiloxane backbone in a terminal position. In one embodiment, the amino-functional polysiloxane is further defined as an amino-functional polydimethylsiloxane. Alternatively, the amino-functional polysiloxane may be further defined as amino-functional polydialkylsiloxane. Further, the amino-functional polysiloxane may include organopolysiloxane groups having the following structures:

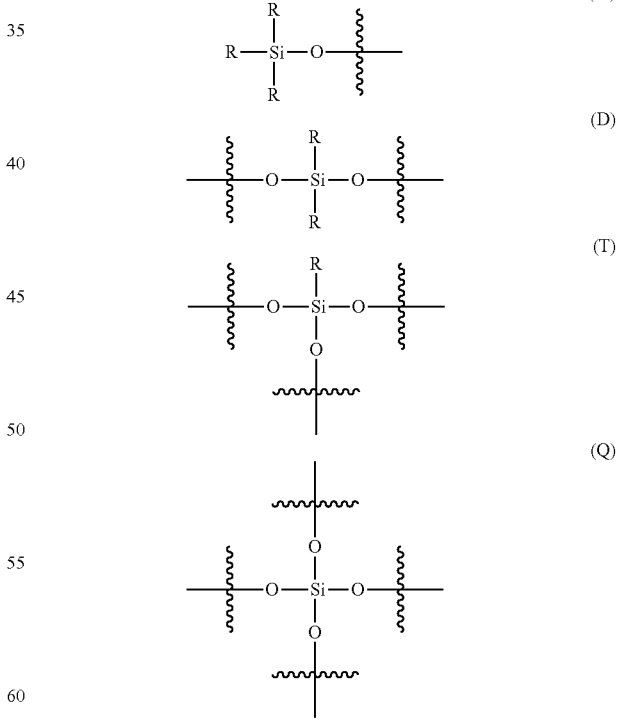

wherein each of M, D, T, and Q independently represent functionality of structural groups of organopolysiloxanes. Specifically, M represents a monofunctional group $R_3SiO_{1/2}$. D represents a difunctional group $R_2SiO_{2/2}$. T represents a trifunctional group $RSiO_{3/2}$. Q represents a tetrafunctional group $SiO_{4/2}$. Of course, the instant disclosure is not limited to the aforementioned amino-functional polysiloxanes and may include any amino-functional polysiloxane known in the art.

The amino-functional polysiloxane typically has a dynamic viscosity of up to one million centipoise (cP), measured at a temperature of 25° C. using dynamic mechanical analysis (DMA) and an oscillatory rheometer equipped with parallel plates. In other embodiments, the amino-functional polysiloxane has a dynamic viscosity of from 350 to 500,000, of from 500 to 120,000, or from 20,000 to 100,000, or of from 40,000 to 60,000, centipoise (cP), measured at a temperature of 25° C. using dynamic mechanical analysis (DMA) and an oscillatory rheometer equipped with parallel plates. However, the amino-functional polysiloxane can have a dynamic viscosity outside of this range if desired.

As set forth above, the silanol and the cyclic silazane typically react to form the amino-functional polysiloxane. In other words, the amino-functional polysiloxane typically is the reaction product of the silanol and the cyclic silazane. Without intending to be bound by any particular theory, it is believed that a lone pair of electrons of an oxygen atom of the silanol attacks a silicon atom of the cyclic silazane in a ring-opening addition reaction to form a new siloxane bond. Then, the bond between the silicon atom and the nitrogen atom of the cyclic silazane is cleaved to form an amine group and provide a monomeric amino-functional siloxane. One possible reaction mechanism is set forth below:

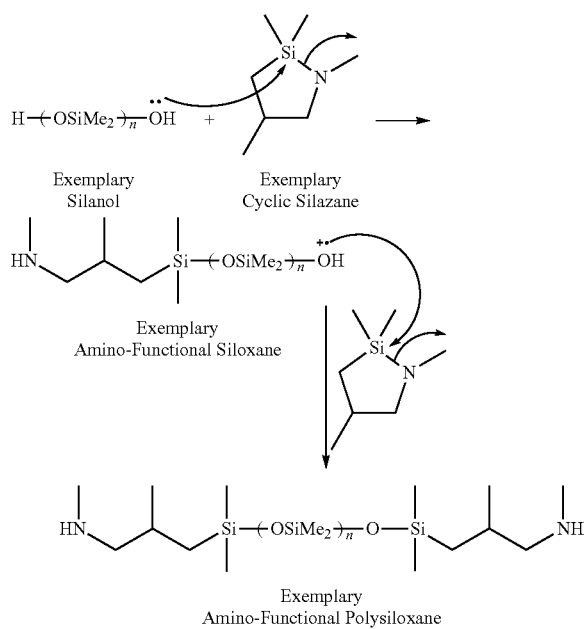

To form the amino-functional polysiloxane, the silanol is typically reacted with the cyclic silazane in a stoichiometric (i.e., molar) ratio of approximately 1:1. However, in alternative embodiments, the silanol is reacted with the cyclic silazane in stoichiometric ratios of 1:9, 2:8, 3:7, and 4:6, and vice versa. However, the amino-functional polysiloxane is not limited to that set forth above and may be any known in the art. The amino-functional polysiloxane typically has a number average molecular weight of from 7,500 to 65,000, of from 10,000 to 50,000, from 20,000 to 40,000, or from 25,000 to 35,000.

Referring back to the isocyanate, the isocyanate typically reacts with the amino-functional polysiloxane in a chain extending reaction. In other words, the isocyanate typically reacts with the amino-functional polysiloxane to extend a polymer chain of the particles. The isocyanate typically includes a diisocyanate and/or a polyisocyanate and may include one or more aliphatic di/poly-isocyanates, aromatic di/poly-isocyanates, heterocyclic di/poly-isocyanates, and combinations thereof. Suitable non-limiting examples of diisocyanates include toluene-2,4-diisocyanate, toluene-2,6-diisocyanate, 1,3-bis(methylisocyanate)cyclohexane, 1,4-bis(methylisocyanate)cyclohexane, 1,4-cyclohexane diisocyanate, diethyldiisocyanatobenzene, 4,4'-diisocyanatodiphenyl ether, 2,4'-diisocyanatodiphenyl sulfide, 3,3'-dimethoxybenzidine-4,4'-diisocyanate, 3,3'-dimethyl-4,4'-diphenylene diisocyanate, 3,3'-dimethyldiphenylmethane-4,4'-diisocyanate, hexamethylene-diisocyanate, isophorone diisocyanate, methyldiphenylmethane-3,4-diisocyanate, 1,1-methylene bis(4-isocyanatocyclohexane). 1,5-naphthalene diisocyanate, 1,3-phenylene diisocyanate, 1,4-phenylene diisocyanate, polymeric diphenylmethane diisocyanate, 2,2,4-trimethylhexamethylene diisocyanate, 2,4,4-trimethylhexamethylene diisocyanate, isomers thereof, and combinations thereof. In one embodiment, the isocyanate is further defined as hexamethylene diisocyanate (HDI).

The isocyanate may also include products which are formed from reacting molecules of aromatic di/poly-isocyanates and/or aromatic di/poly-isocyanates with each other. These products may include, but are not limited to, ureas, biurets, allophanates, carbodiimides, uretonimines, isocyanurates, and combinations thereof. The isocyanate is typically reacted with the amino-functional polysiloxane in a stoichiometric (i.e., molar) ratio of approximately 1:1. However, in alternative embodiments, the isocyanate is reacted with the amino-functional polysiloxane in stoichiometric ratios of 1:9, 2:8, 3:7, and 4:6, and vice versa. Without intending to be bound by any particular theory, it is believed that increasing a stoichiometric amount of the isocyanate increases a number average molecular weight of the particles of this disclosure. It is also believed that if the isocyanate has more than two isocyanate groups (e.g. a trifunctional- or poly-functional-isocyanate), the isocyanate may act as both a chain extender and a cross-linker. In other words, the isocyanate may react with the amino-functional polysiloxane in a chain extending reaction and also react with the amino-functional polysiloxane to cross-link the particles. Most typically, the isocyanate acts as a (linear) chain extender.

In addition, it is believed that the isocyanate reacts (polymerizes) with the amino-functional polysiloxane in a urea forming addition reaction to form the particles. In one embodiment, the reaction of the amino-functional polysiloxane and the isocyanate forms an AB block copolymer having polysiloxane groups attached through urea linkages. A typical generic urea forming addition reaction mechanism, including one type of amino-functional polysiloxane, is set forth below:

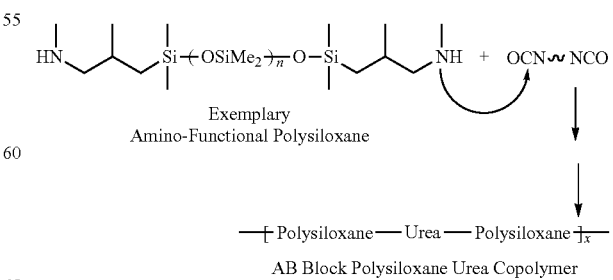

wherein x is a positive integer.

Referring back to the method, in one embodiment, the method includes the step of reacting the silanol and the cyclic silazane to form the amino-functional polysiloxane. This step of reacting may occur within any type of emulsion known in the art or may occur in the absence of an emulsion. Typically, the step of reacting occurs in the absence of an emulsion. The step of reacting the silanol and the cyclic silazane may occur via the mechanism described above in a ring opening addition reaction or by another mechanism.

In another embodiment, the method includes the step of forming the o/w emulsion including the amino-functional polysiloxane. The amino-functional polysiloxane may be formed using the aforementioned step of reacting or through any other method known in the art. The step of forming the o/w emulsion may be further defined as first forming a water-in-oil (w/o) emulsion including the amino-functional polysiloxane and less than 0.1 weight percent of the hydrophobic costabilizer and phase inverting the w/o emulsion to form the o/w emulsion. As described above, minimizing the amount of the hydrophobic costabilizer decreases production costs and times needed to form the particles. In one embodiment, the instant disclosure is free of the hydrophobic costabilizer.

The w/o emulsion may be phase inverted to form the o/w emulsion by any means known in the art including, but not limited to, use of surfactants, mixing, and/or shear (e.g. a shearing force). Alternatively, the step of forming the o/w emulsion may be further defined as first forming a water-in-oil (w/o) emulsion including the amino-functional polysiloxane and less than 0.1 weight percent of the hydrophobic costabilizer and applying shear (e.g. a shearing force) to the w/o emulsion to form the o/w emulsion. Shear may be applied to the w/o emulsion using any technique or apparatus known in the art including, but not limited to, by spinning, by vortexing, by centrifuging, and/or by using a colloid mill, a Sonolator®, a homogenizer, a Microfluidizer®, ribbon mixers, plow mixers, fluidizing paddle mixers, sigma blade mixers, tumble blenders, vortex mixers, feed mixers, vertical mixers, horizontal mixers, a SpeedMixer™, and combinations thereof.

Alternatively, the step of forming the o/w emulsion may include emulsifying the silanol, cyclic silazane, amino-functional polysiloxane, isocyanate, particles and/or water or another liquid. The step of emulsifying may form the o/w emulsion but may not form the particles. The surfactant and/or thickener may be added prior to, concurrent with, or after emulsification of the silanol, cyclic silazane, amino-functional polysiloxane, isocyanate, particles and/or water or another liquid.

In yet another embodiment, the method includes the step of combining the amino-functional polysiloxane and the isocyanate in the o/w emulsion to react and form the particles. One example of such a reaction is set forth above. Typically, in this embodiment, the emulsion of the amino-functional polysiloxane and the isocyanate react for a time of 0.5 to 24 hours at room temperature or a higher temperature to form the particles. However, the disclosure is not limited to these times or temperatures. Without intending to be bound by any particular theory, it is believed that the isocyanate migrates through the water of the o/w emulsion to react with the amino-functional polysiloxane. Heating the o/w emulsion to a temperature of less than or equal to about 100° C. may increase a rate of reaction. In addition, any amount of isocyanate that does not react with the amino-functional polysiloxane may react with water, thereby decomposing the isocyanate and forming carbon dioxide gas which increases safety of the instant method.

In addition to the method described above, the instant disclosure also provides the o/w emulsion itself. The o/w emulsion includes the particles having the diameter of at least 30 nanometers. The particles of the o/w emulsion may be formed using any or all of the method steps described in detail above. Typically, to form the o/w emulsion, the silanol and the cyclic silazane react to form the amino-functional polysiloxane which is then reacted with the isocyanate in the o/w emulsion to form the particles.

In the method of this disclosure, it is believed that the isocyanate migrates through the aqueous water phase of the o/w emulsion to react with the amino-functional polysiloxane. In other words, the reaction of the Isocyanate and the amino-functional polysiloxane is thought to be kinetically favored (e.g. 100 times faster) over reaction of the isocyanate with water and/or the silanol. Further, in this method, any amount of isocyanate that does not react with the amino-functional polysiloxane may react with water, thereby breaking apart the isocyanate and forming carbon dioxide gas which increases safety of the instant method.

In addition to the o/w emulsion and the method described above, the instant disclosure also provides a personal care composition (e.g. a cosmetic composition or toiletry composition) including the o/w emulsion and the particles of this disclosure. The o/w emulsion of the instant disclosure is useful in most known applications for silicone emulsions, for example in personal care applications such as on hair, skin, mucous membrane or teeth. In many of these applications, the o/w emulsion is lubricious and improves properties of skin creams, skin care lotions, moisturizers, facial treatments such as acne or wrinkle removers, personal and facial cleansers, bath oils, perfumes, fragrances, colognes, sachets, sunscreens, pre-shave and after shave lotions, shaving soaps and shaving lathers. The o/w emulsion can likewise be used in hair shampoos, hair conditioners, hair sprays, mousses, permanents, depilatories, and cuticle coats, for example to provide styling and conditioning benefits. In cosmetics, the o/w emulsion may function as a leveling and spreading agent for pigment in make-ups, color cosmetics, foundations, blushes, lipsticks, eye liners, mascaras, oil removers, color cosmetic removers and powders. The o/w emulsion may also be useful as a delivery system for oil and water soluble substances such as vitamins, organic sunscreens, ceramides, pharmaceuticals and the like. When compounded into sticks, gels, lotions aerosols and roll-ons, the o/w emulsion may impart a dry silky-smooth payout. The o/w emulsion may also be mixed with deposition polymers, surfactants, detergents, antibacterials, anti-dandruffs, foam boosters, proteins, moisturizing agents, suspending agents, opacifiers, perfumes, coloring agents, plant extracts, polymers, and other conventional care ingredients. In one embodiment, the o/w emulsion is included in a water based composition that is selected from the group of cosmetic compositions, coating compositions, and combinations thereof. The o/w emulsion may be used in personal care products in amounts of from 0.01 to about 50, and more typically in amounts of from 0.1 to 25, weight percent of a personal care product.

The o/w emulsion may also be useful for numerous other applications such as in a textile treatment composition. In this disclosure, the textile may be woven or non-woven or may include both woven and non-woven segments. In one embodiment, the textile is selected from the group of fiberglass, polyester, polyethylene, polypropylene, nylon, polyethylene terephthalate, and combinations thereof. Of course, it is to be understood that the textile is not limited to aforementioned types of woven and non-woven textiles and may include any woven or non-woven textile known in the art.

As is known in the art, woven textiles are typically cloths that are formed by weaving and that stretch in bias directions. As is also known in the art, non-woven textiles are neither woven nor knit and are typically manufactured by putting individual fibers together in the form of a sheet or web, and then binding them either mechanically, with an adhesive, or thermally by melting a binder onto the textile. Non-woven textiles may include staple non-woven textiles and spunlaid non-woven textiles. Staple non-woven textiles are typically made by spinning fibers that are spread in a uniform web and then bonded by using either resin or heat. Spunlaid non-woven textiles are typically made in one continuous process by spinning fibers directly disposed into a web. The spunlaid process can be combined with a meltblowing process to form a SMS (spun-melt-spun) non-woven textile.

Non-woven textiles may also include films and fibrillates and can be formed using serration or vacuum-forming to form patterned holes. Fiberglass non-woven textiles typically are one of two types including wet laid mats having wet-chopped, denier fibers having 6 to 20 micrometer diameters or flame attenuated mats having discontinuous denier fibers having 0.1 to 6 micrometer diameters.

The textile treatment composition may be further defined as a leather lubricator, a fabric softener, a release agent, a stain preventative, a stain treatment, and the like. The o/w emulsion may be used in the textile treatment composition in amounts of from 0.01 to about 50, and more typically in amounts of from 0.1 to 25, weight percent of a personal care product.

This disclosure also provides a coating and/or film comprising the particles described above. For example, the coating may be, include, consist essentially of, or consist of, the particles. In one embodiment, the terminology "consists essentially of" describes a coating that is free of polymers and/or polysiloxanes and/or silicones, that are not the particles. In other embodiments, the coating includes from 0.1 to approximately 100 wt % of the particles. Each and every value and range of values between 0.1 and approximately 100 wt % is herein expressly contemplated. The particles may be the coating itself or they may be included in the coating as an ingredient or additive. The coating may be water based or oil based or a combination thereof. In various embodiments, the coating is water reducible. The coating may be, e.g. a free standing film, or may be disposed on a substrate, e.g. metal, glass, polymer, plastic, wood, etc. The coating and/or film may have a thickness of from 1 nanometer to 1 inch. In various embodiments, the coating and/or film has a thickness of from 1 to 50 micrometers. Each and every value and range of values between 1 nanometer and 1 inch is herein expressly contemplated. The coating and/or film may be described as protective, architectural, building, automotive, aerospace, construction, etc.

EXAMPLES

Example 1

To form Emulsion 1, 90 grams of a silanol, which, in this Example, is a polydimethylsiloxane that has two terminal —OH groups, a viscosity of approximately 50,000 cP and a number average molecular weight of approximately 61,100, are added to a SpeedMixer™ max 100 gram cup followed by 0.42 grams of N-1,1,2,4-tetramethyl-1-sila-2-azacyclopentane, a cyclic silazane. The cup is closed and placed into a DAC 150 SpeedMixer™ and spun at 3,000 rpm for 20 seconds. The cup and its contents are allowed to remain undisturbed for 24 hours at ambient laboratory conditions to allow the silanol and the cyclic silazane to react to form an amino-functional polydimethylsiloxane. After 24 hours, 55 g of the amino-functional polydimethylsiloxane are removed and added to a second max 100 g cup. Subsequently, 0.83 grams of polyoxyethylene (4) lauryl ether (commercially available under the trade name of Brij® 30), as a surfactant, are added to the cup followed by 1.21 grams of a 72% aqueous solution of polyoxyethylene (23) lauryl ether (commercially available under the trade name of Brij® 35L), as a second surfactant, Then, 0.6 grams of deionized (DI) water are added to the cup. The addition of the surfactants and the water to the amino-functional polydimethylsiloxane forms a water-in-oil (w/o) emulsion. The cup is then placed into a DAC 150 SpeedMixer™ and spun at 3,000 rpm for 20 seconds to phase invert the w/o emulsion into an o/w emulsion. The cup is removed from the mixer and the walls are scraped with a spatula. The contents of the cup form a thick paste that is an oil-in-water emulsion of the amino-functional polydimethylsiloxane in water that had inverted from the previous w/o emulsion (before spinning). After scraping the walls of the cup, the cup is spun a second time at 3,000 rpm for 20 seconds. 1 gram of DI water is then added to the cup which is subsequently spun yet again for 20 seconds at 3,000 rpm. Then, 2 grams of water are added in the same manner as above followed by 3 grams and 5 grams of DI water, with the cup spun 20 seconds between each water addition at 3,000 rpm. Water is added up to a total of 33.6 grams, excluding the first addition of 0.6 grams of water. The addition of the water forms an approximately 60% active, aqueous, oil-in-water (o/w) white emulsion of a polydimethylsiloxane having N-methylaminoisobutyl substituted end groups (Emulsion 1).

Subsequently, 0.16 grams of hexamethylene diisocyanate are added to the cup drop wise using a pipette. The HDI forms drops that float on a surface of the o/w emulsion. The cup is then placed into the SpeedMixer® and spun for 20 seconds at 3,500 rpm. The cup and its contents then remain undisturbed for 24 hours at ambient laboratory conditions to allow the isocyanate to react with the amino-functional polydimethylsiloxane to form the Particles 1. After 24 hours, a 10 gram portion of the o/w emulsion is poured into a 60 mm plastic Petri dish and allowed to dry for 24 hours at ambient laboratory conditions to form a viscous gum. The viscous gum is evaluated using dynamic mechanical analysis (DMA) and an oscillatory rheometer equipped with parallel plates and found to have a viscosity of approximately 240,000 Pa-sec. @$10^{-1}$ Hz. A plot of the DMA results is set forth in FIG. 1. An aliquot of the o/w emulsion is also subjected to particle size analysis using laser light scattering. The mean particle size (diameter) of Particles 1 is approximately 0.956 µm with approximately 90% of the particles having a size of less than 1.27 µm, as determined by light scattering using a Nanotrac® particle size analyzer.

Example 2

To form Emulsion 2, 20 grams of a polydimethylsiloxane fluid, representing the amino-functional polysiloxane of this disclosure, having a degree of polymerization (DP) of approximately 100, and terminated with N-methylaminoisobutyl dimethylsiloxy groups, are added to a 50 ml jar. Then, 0.25 grams of polyoxyethylene (4) lauryl ether (commercially available under the trade name of Brij® 30) as surfactant are added to the jar followed by 0.45 grams of a 72% aqueous solution of polyoxyethylene (23) lauryl ether (commercially available under the trade name of Brij® 35L) as a second surfactant and 19.3 grams of deionized (DI) water. An ultrasonic processor probe is then immersed in the jar approximately 1 cm deep. The probe is then energized to full power (550 W) and polydimethylsiloxane, surfactants, and water turned white within several seconds. Ultrasonic processing is then continued for 30 seconds after which energy to the probe is arrested and the probe is removed from the jar. The jar is then shaken by hand for 10 seconds and cooled under running water for several minutes. Subsequently, the probe is returned to the jar and re-activated for an additional 30 seconds. After 30 seconds, the energy to the probe is arrested and the probe is removed from the jar. Then, the jar is shaken and cooled with running water. The probe is then re-inserted into the jar and ultrasonic processing is continued for an additional 30 seconds such that the total ultrasonic processing time is approximately 1.5 minutes. The ultrasonic processing formed 38 grams of a 50% active, aqueous, oil-in-water (o/w) emulsion of polydimethylsiloxane having terminal N-methylaminoisobutyl groups (Emulsion 2).

Figure 2:
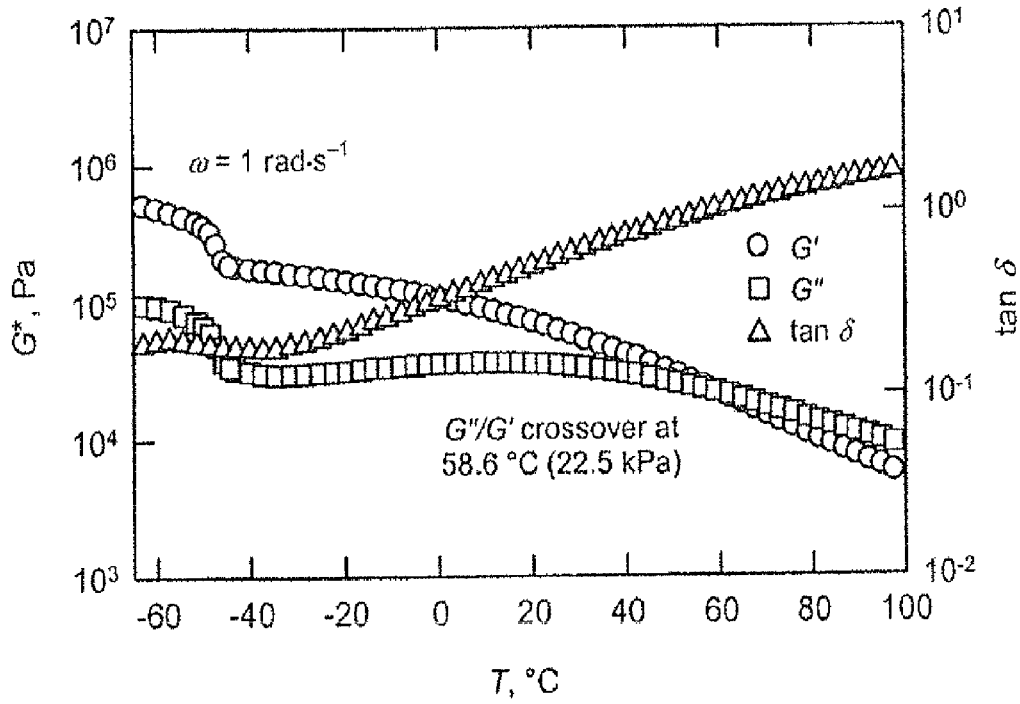
FIG. 2 is a dynamic mechanical analysis/rheological profile of the polymer of Example 2.

Subsequently, 0.46 grams of hexamethylene diisocyanate are added to the cup drop wise using a pipette. The cup is then placed into a SpeedMixer® DAC 150 and spun at 3,000 rpm for 20 seconds. The cup and its contents remain undisturbed for 24 hours at ambient laboratory conditions to allow the isocyanate to react with the polydimethylsiloxane and form the Particles 2. After 24 hours, a 15 gram portion of Emulsion 2 is poured into a 60 mm plastic Petri dish and allowed to dry for 24 hours at ambient laboratory conditions to form a rubbery polymer. A portion of the rubbery polymer is subjected to DMA using an oscillatory rheometer equipped with parallel plates and found to have a viscosity of approximately 800,000 Pa-sec. measured at a temperature of 25° C. and at $10^{-1}$ Hertz (Hz) using dynamic mechanical analysis (DMA) and an oscillatory rheometer equipped with parallel plates. Results of a temperature sweep at $10^{-1}$ Hz of the rubbery polymer from Emulsion 2 are set forth in FIG. 2.

Example 3

Preparation of Polymers

Polymer A is prepared by first weighing into a two quart round glass jar 1031.3 grams of a polydimethylsiloxane linear polymer having terminal —OH groups, a viscosity of approximately 50,000 mPa-sec. cP and a number average molecular weight of approximately 61,100. Next 4.80 grams of N-1,1,2,4-tetramethyl-1-sila-2-azacyclopentane, a cyclic silazane, are weighed into the jar. The cap is secured and the jar is rolled at a slow speed for 24 hours using a jar rolling apparatus under ambient laboratory conditions to form Polymer A. Polymer A is a polydimethylsiloxane polymer (Mn ~61,100) having terminal secondary amino groups. The viscosity of Polymer A is about the same as the starting siloxane.

Polymer B is prepared by a similar method of Polymer 1, except a higher ratio of cyclic silazane to SiOH polymer is used. 1159.7 grams of the same polymer used to prepare Polymer 1 are weighed into a two quart round glass jar. Next 5.44 grams of N-1,1,2,4-tetramethyl-1-sila-2-azacyclopentane (cyclic silazane) are weighed into the jar. The cap is secured on the jar and the jar is rolled at a slow speed for 24 hours using a jar rolling apparatus under ambient laboratory conditions to form Polymer B. Polymer B is a polydimethylsiloxane polymer (Mn ~61,100) having terminal, secondary amino groups. Polymer B also has about the same viscosity as the starting siloxane.

Polymer C is also prepared by the same method of Polymer 1 except a different molecular weight SiOH polymer is used. 780.08 g of a polydimethylsiloxane polymer having terminal —OH groups, a viscosity of approximately 2,000 mPa-sec. and a number average molecular weight of approximately 23,300 is weighed into a 1 quart jar followed by 9.57 g of N-1,1,2,4-tetramethyl-1-sila-2-azacyclopentane. The cap is secured to the jar and the jar is rolled at a slow speed for 24 hours using a jar roller under ambient laboratory conditions to form Polymer C. Polymer C is a polydimethylsiloxane polymer (Mn ~23,300) having terminal secondary amino groups. The viscosity of Polymer C is about the same as the starting siloxane.

Preparation of Emulsions

Example 3A 60 grams of Polymer A are weighed into a max 100 cup followed by 0.96 grams of Brij 30 and 1.80 grams of Brij 35L and 1.0 g of DI water. The cup is closed and placed inside a SpeedMixer® DAC-150 and the cup is spun for 30 seconds at maximum speed (approximately 3,500 RPM). The cup is opened and the walls of the cup are scraped with a spatula after which the cup is closed and placed back into the mixer and spun for an additional 30 seconds at maximum speed. The contents of the cup are diluted with a total of 25.4 grams of DI water in four increments starting with 2.5 grams, then 5.0 grams, then 7.5 grams and finally 10.4 grams. The cup is spun for 20 seconds at maximum speed after each dilution. After the final dilution has been made and the cup spun the final time, 0.174 grams of HDI, hexamethylene diisocyanate, is added drop wise using a pipette. The cup is closed and spun at maximum speed for two cycles of 30 seconds each with a waiting period between spin cycles of approximately two minutes. The cup is allowed to remain undisturbed at ambient laboratory conditions for 24 hours after which particle size is determined (Malvern® 2000) and polymer is harvested for rheology testing. The composition is an oil-in-water aqueous emulsion of high viscosity PDMS having a silicone content of approximately 67 percent by weight and a mean particle size (Dv50) of 0.64 um with 90 percent of the particles being less than 1.07 um.

Harvesting of Polymer

Approximately 8 grams of the emulsion described immediately above is weighed into a Max 40 cup. Next isopropyl alcohol (IPA) is added to the cup using a squeeze bottle until the cup is almost full (approximately 30 grams of IPA). The cup is closed and spun at maximum speed in a SpeedMixer® DAC-150 for 30 seconds. The cup is opened and the alcohol layer is decanted (and discarded) from the polymer which is at the bottom of the cup. The polymer is rinsed with additional IPA then it is transferred to a 100 mm diameter plastic Petri dish (open) and placed into an air circulating oven maintained at 70 C. The polymer is allowed to dry in the oven for 48 hours. Rheological properties of the polymer are determined using a TA Instruments ARES® (New Castle Del.) rheometer equipped with 25 mm diameter parallel plates and operated at 25 degrees C. in a frequency sweep mode from 0.01 Hz to 80 Hz using a dynamic strain of 10 percent. This polymer has a viscosity of approximately 13,600 Pa-sec. at 0.01 Hz.

Example 3B

Figure 3:
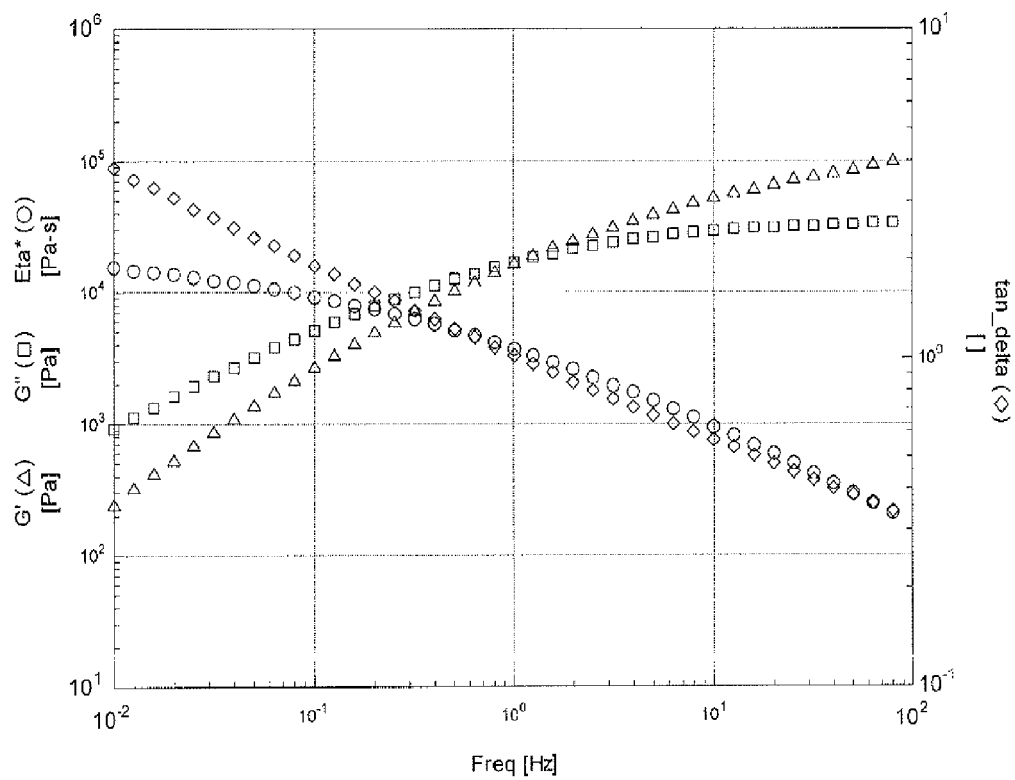
FIG. 3 is a dynamic mechanical analysis/rheological profile of the polymer of Example 3B.

An emulsion is prepared using the same polymer and same procedure as that of Example 2A except that particle size of the emulsion is larger. 60 grams of Polymer A are weighed into a max 100 cup followed by 0.96 grams of Brij® 30 and 1.80 grams of Brij® 35L and 3.90 grams of DI water. The cup is closed and placed inside a SpeedMixer® DAC-ISO and the cup is spun for 30 seconds at maximum speed (approximately 3,500 RPM). The cup is opened and the walls of the cup are scraped with a spatula after which the cup is closed and placed back into the mixer and spun for an additional 30 seconds at maximum speed. The contents of the cup are diluted with a total of 25.65 grams of DI water in four increments starting with 2.5 grams, then 5.0 grams then 7.5 grams and finally 10.65 grams. The cup is spun for 20 seconds at maximum speed after each dilution. After the final dilution is made and the cup spun the final time, 0.176 grams of HDI, hexamethylene diisocyanate, is added drop wise using a pipette. The cup is closed and spun at maximum speed for two cycles of 60 seconds each with a waiting period between spin cycles of approximately two minutes. The cup is allowed to remain undisturbed at ambient laboratory conditions for 24 hours after which particle size is determined (Malvern® 2000) and polymer is harvested for rheology testing. This composition consists of an oil-in-water aqueous emulsion of high viscosity PDMS having a silicone content of approximately 65 percent by weight and a mean particle size (Dv50) of 3.36 um with 90 percent of the particles being less than 5.24 um. The polymer from this emulsion is harvested by the procedure described for Example 2A and this polymer has a viscosity of approximately 14,800 Pa-sec. at 0.01 Hz. A rheological profile of this polymer is set forth in FIG. 3.

Example 3C

An emulsion is prepared using the same procedure as that of Example 2B except that Polymer B is used in place of Polymer A. 60 grams of Polymer B are weighed into a max 100 cup followed by 0.96 grams of Brij® 30, 1.81 grams of Brij® 35L and 3.90 grams of DI water. The cup is closed and placed inside a SpeedMixer® DAC-150 and the cup is spun for 30 seconds at maximum speed (approximately 3500 RPM). The cup is opened and the walls of the cup are scraped with a spatula after which the cup is closed and placed back into the mixer and spun for an additional 30 seconds at maximum speed. The contents of the cup are diluted with a total of 25.65 grams of DI water in four increments starting with 2.5 grams, then 5.0 grams then 7.5 grams and finally 10.65 grams. The cup is spun for 20 seconds at maximum speed after each dilution. After the final dilution is made and the cup is spun the final time, 0.174 grams of HDI, hexamethylene diisocyanate, is added drop wise using a pipette. The cup is closed and spun at maximum speed for two cycles of 60 seconds each with a waiting period between spin cycles of approximately two minutes. The cup is allowed to remain undisturbed at ambient laboratory conditions for 24 hours after which particle size is determined (Malvern® 2000) and polymer is harvested for rheology testing. This composition consists of an oil-in-water aqueous emulsion of high viscosity PDMS having a silicone content of approximately 65 percent by weight and a mean particle size (Dv50) of 3.07 um with 90 percent of the particles being less than 4.71 um.

Figure 4:
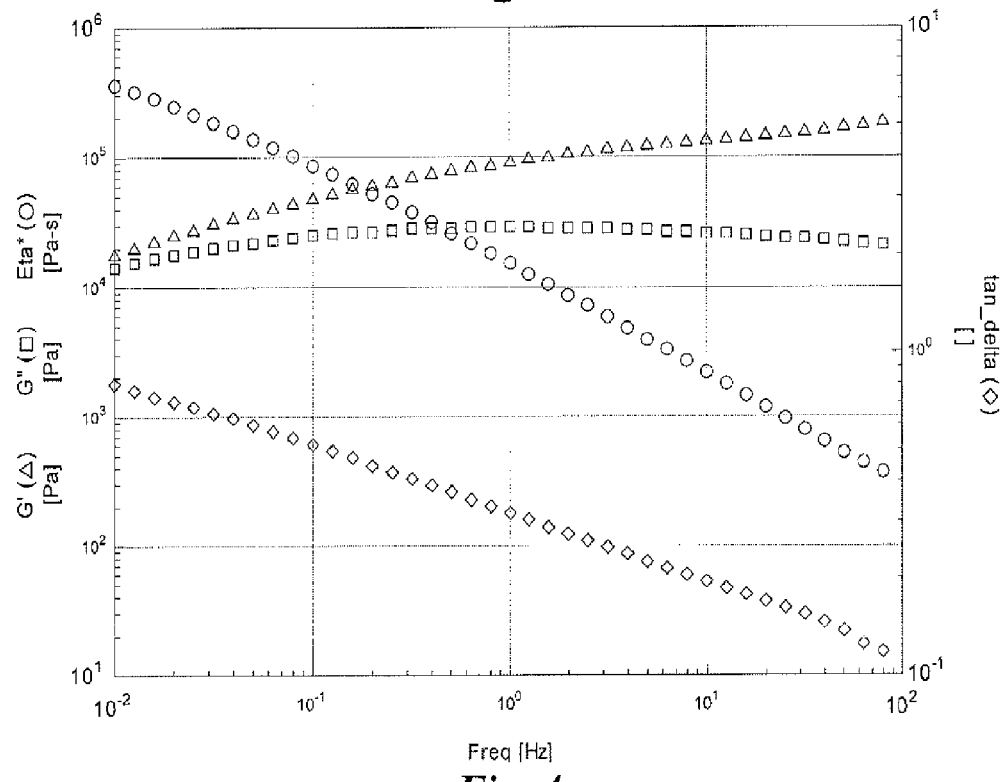
FIG. 4 is a dynamic mechanical analysis/rheological profile of the polymer of Example 3C.

The polymer is harvested in the same manner as that used for Example 2A. The polymer has a viscosity of approximately 62,900 Pa-sec. at 0.01 Hz. A rheological profile of this polymer is set forth in FIG. 4.

Example 3D

Figure 5:
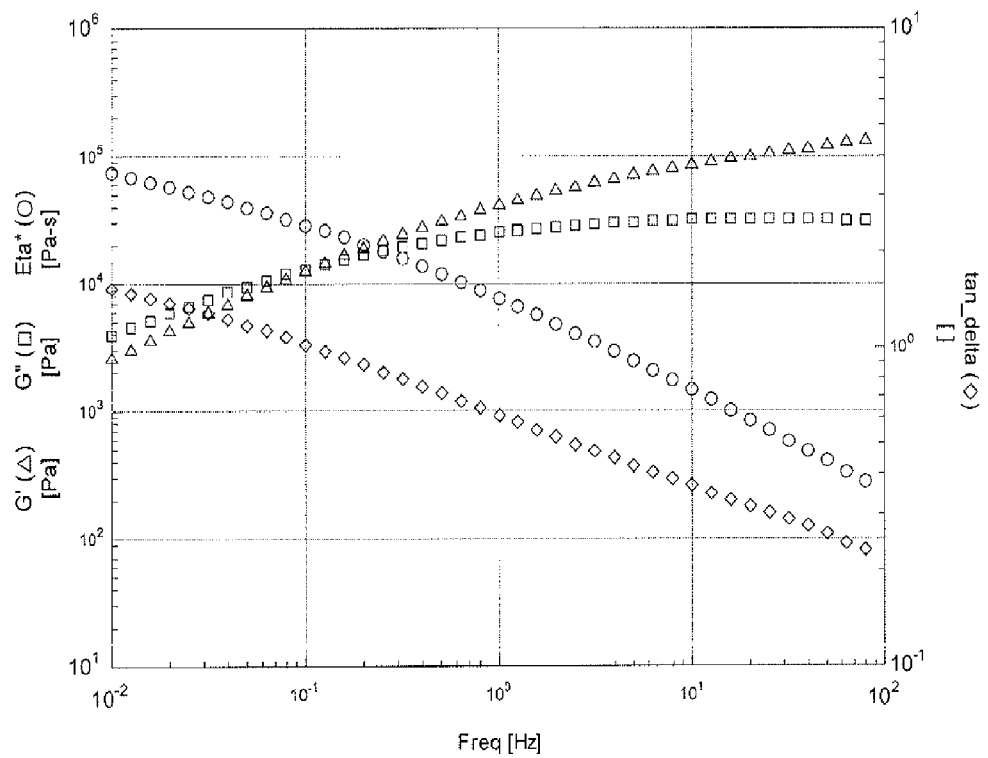
FIG. 5 is a dynamic mechanical analysis/rheological profile of the polymer of Example 3D.

An emulsion is prepared using the same procedure and ingredients of Example 2C except that 0.227 g of isophorone diisocyanate (IPDI) is substituted for 0.169 g of HDI that is used in the composition of Example 2c. This emulsion has a mean particle size (Dv50) of 3.43 um with 90% of the particles being less than 5.29 um. The emulsion also has a silicone content of approximately 65 percent. The polymer is harvested in the same manner as that used in Example 2A. The polymer has a viscosity of about 227,000 Pa-sec. at 0.01 Hz. A rheological profile of this polymer is set forth in FIG. 5.

Example 3E

Figure 6:
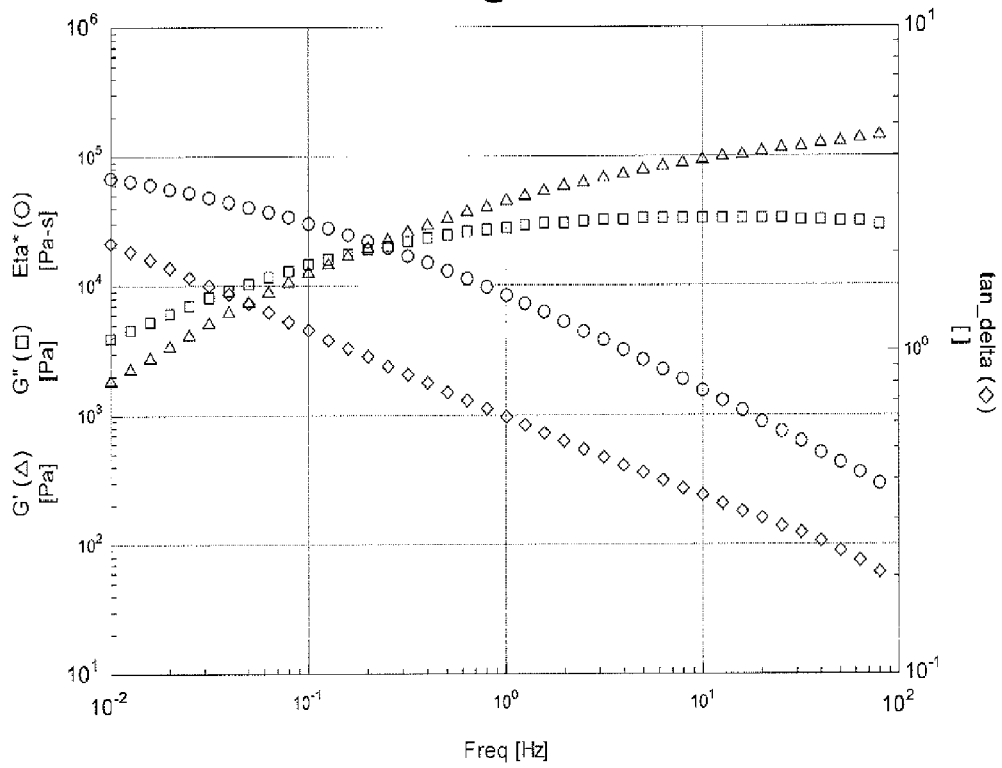
FIG. 6 is a dynamic mechanical analysis/rheological profile of the polymer of Example 3E.

An emulsion is prepared using the same procedure of Example 2C except that a different polymer and different surfactants are used. 60 g of Polymer C are weighed into a max 100 cup followed by 0.96 grams of Tergitol® 15-S-5, 1.80 grams of Tergitol® 15-S-40 (70 percent in water) and 0.5 grams of DI water. The cup is closed and placed inside a SpeedMixer® DAC-150 and the cup is spun for 30 seconds at maximum speed (approximately 3,500 RPM). The cup is opened and the walls of the cup are scraped with a spatula after which the cup is closed and placed back into the mixer and spun for an additional 30 seconds at maximum speed. The contents of the cup are diluted with a total of 29.05 grams of DI water in four increments starting with 2.5 grams, then 5.0 grams then 7.5 grams and finally 14.05 grams. The cup is spun for 20 seconds at maximum speed after each dilution. After the final dilution is made and the cup is spun the final time, 0.425 grams of HDI, hexamethylene diisocyanate, is added drop wise using a pipette. The cup is closed and spun at maximum speed for two cycles of 60 seconds each with a waiting period between spin cycles of approximately two minutes. The cup is allowed to remain undisturbed at ambient laboratory conditions for 24 hours after which particle size is determined (Malvern® 2000) and polymer is harvested for rheology testing. This composition consists of an oil-in-water aqueous emulsion of high viscosity PDMS having a silicone content of approximately 65 percent by weight and a mean particle size (Dv50) of 2.48 um with 90 percent of the particles being less than 4.01 um. Polymer is harvested using the procedure as described in Example 2a. Polymer viscosity is about 62,200 Pa-sec. at 0.01 Hz. A rheological profile of this polymer is set forth in FIG. 6.

Comparative Example 4

An amino functional terminated polydimethylsiloxane is first prepared by weighing 1482.0 g of a terminal OH functional polydimethylsiloxane polymer having a viscosity of approximately 50,000 cP and a number average molecular weight of approximately 61,100. Next 7.10 grams of N-1,1,2,4-tetramethyl-1-sila-2-azacyclopentane, a cyclic silazane, is weighed into the jar. The cap is secured and the jar is rolled at a slow speed for 24 hours using a jar roller under ambient laboratory conditions to form the comparative polymer. This comparative polymer is a polydimethylsiloxane having terminal secondary amino groups and has a viscosity about the same as that of the starting polymer (approximately 50,000 cP). 20 g of this composition is weighed into a Max 40 cup followed by 0.599 grams of a 10 percent solution of HDI, hexamethylene diisocyanate, dissolved in polydimethylsiloxane fluid (Dow Corning@1.5 cSt. 200 Fluid). The cup is placed inside a SpeeodMixer® DAC-150 mixer and the cup is spun at maximum speed for 20 seconds. The cup is allowed to remain undisturbed for four hours at ambient laboratory conditions.

Emulsification of the resulting high viscosity polymer is attempted next. The polymer is broken up with a spatula into centimeter size pieces and 2.0 grams is weighed into a Max 10 cup. 0.06 grams of Tergitol® 15-S-5 and 0.10 grams of Tergitol® 15-S-40 (70 percent aqueous solution) are weighed into the cup next followed by 0.60 grams of DI water. The cup is spun for sixty seconds at maximum speed using the SpeedMixer® DAC-150. The cup is opened and the contents inspected. The contents consist of a clear liquid surrounding large pieces of clear polymer. The cup is closed and spun again and the contents inspected. The appearance does not change and the quantity of large pieces of polymer also appears to be unchanged. The procedure is repeated two more times with the same result. The composition basically does not become an emulsion.

The composition is transferred into a 15 ml wide mouth vial with an additional 4.5 grams of DI water. The new composition is subjected to ultrasonication by immersing an ultrasonic probe (12 mm diameter) into the liquid 1 cm under the surface and energizing the probe at one half power (Mixonix 3000 Sonicator® rated at 500 W maximum power) for 20 seconds. The probe is removed from the vial and the vial is cooled in running cold water for one minute. The probe is reinserted under the liquid and probe is energized at one-half power for an additional 20 seconds. This procedure is repeated so that the mixture receives a total of 60 seconds of ultrasonication. Inspection of the mixture after it had remained undisturbed for ten minutes so that the foam could subside reveals it to consist of a clear liquid with numerous pieces of clear high viscosity polymer within it. In other words, the composition does not become an emulsion as the polymer does not become dispersed in the water.

A second attempt is made to disperse the high viscosity polymer into an aqueous emulsion using a different surfactant and also a hydrophobic co-stabilizer. 2.0 grams of the above described high viscosity polymer is weighed into a Max 10 cup followed by 0.4 grams of a 20 percent aqueous solution of sodium dodecyl sulfate. 0.08 grams of hexadecane is added and finally 0.5 grams of DI water was added. The cup is closed and spun for 30 seconds at maximum speed using a SpeedMixer® DAC-150 mixer. The contents of the cup are inspected to reveal clear polymer pieces in a clear liquid. The cup is spun for an additional 30 seconds with the same result. The contents of the cup are transferred into a 15 ml wide mouth vial with an additional 5.0 grams of DI water. The contents of the vial are subjected to ultrasonication at 20 second intervals as described above except total time of this procedure is two minutes. The resulting composition consists of a slightly opaque liquid with clear polymer pieces within. The polymer pieces appear to be of the same size before the ultrasonic processing began. The polymer pieces are separated from the liquid and washed with water and dried in a 70 C oven for two hours and their weight is now 1.99 grams. This indicates that the polymer essentially does not emulsify.

The formation of the emulsions and particles as described in Examples 1-3 above, demonstrates that the instant disclosure efficiently forms particles in the oil-in-water emulsion. The particles can be handled easily, accurately and efficiently checked for quality and customized to desired physical and chemical properties. Further, the above Examples demonstrate that highly viscous particles can be formed in an oil-in-water emulsion with a cost effective and simple method. In addition, any amount of isocyanate that does not react with the amino-functional polysiloxane reacts with water, thereby decomposing the isocyanate and forming carbon dioxide gas which increases safety of the instant method.

The disclosure allows for preparation of a wide range of polymer viscosities within in the emulsion particles. The advantage of preparing the polymer particles described in this disclosure in an emulsion is that extremely high viscosity polymers can be handled with relative ease in emulsion form as such emulsions can be made to have low viscosities and hence are pourable liquids.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A method of forming particles having an average diameter of at least 30 nanometers, said method comprising the steps of:
    A. reacting a silanol and a cyclic silazane to form an amino-functional polysiloxane;
    B. forming an oil-in-water emulsion comprising the amino-functional polysiloxane and less than 0.1 weight percent of a hydrophobic costabilizer;
    C. combining the amino-functional polysiloxane and an isocyanate in the oil-in-water emulsion to react and form the particles having the average diameter of at least 30 nanometers.

2. The method of claim 1 wherein the step of forming the oil-in-water emulsion is further defined as forming a water-in-oil emulsion comprising the amino-functional polysiloxane and less than 0.1 weight percent of a hydrophobic costabilizer and phase inverting the water-in-oil emulsion to form the oil-in-water emulsion.

3. The method of claim 1 wherein the step of forming the oil-in-water emulsion is further defined as forming a water-in-oil emulsion comprising the amino-functional polysiloxane and less than 0.1 weight percent of a hydrophobic costabilizer and applying shear to the water-in-oil emulsion to form the oil-in-water emulsion.

4. The method of claim 1 wherein the silanol has the chemical formula $H(OSiR^1R^2)_nOH$ wherein each of $R^1$ and $R^2$ is independently selected from the group of alkyl groups, cyclic alkyl groups, aromatic groups, and combinations thereof and n is a number of from 1 to 2,000.

5. The method of claim 4 wherein n is a number of from 200 to 900.

6. The method of claim 4 wherein $R^1$ and $R^2$ are both methyl groups.

7. The method of claim 1 wherein the cyclic silazane is further defined as 1,1,2,4-tetramethyl-1-sila-2-azacyclopentane.

8. The method of claim 1 wherein the amino-functional polysiloxane is further defined as an amino-functional polydimethylsiloxane.

9. The method of claim 1 wherein the particles have an average diameter of from greater than 500 nanometers up to 1,000 nanometers.

10. The method of claim 1 wherein the particles have a dynamic viscosity of at least 100 million centipoise measured at a temperature of 25° C. and at $10^{-1}$ Hertz.

11. The method of claim 1 wherein the oil-in-water emulsion is free of the hydrophobic costabilizer, the silanol has the chemical formula $H(OSiR^1R^2)_nOH$ wherein each of $R^1$ and $R^2$ are methyl groups, and n is a number from 700 to 900, the cyclic silazane is further defined as 1,1,2,4-tetramethyl-1-sila-2-azacyclopentane, the amino-functional polysiloxane is further defined as an amino-functional polydimethylsiloxane, the isocyanate is further defined as hexamethylene diisocyanate, and the particles have an average diameter of greater than 500 nanometers and up to 1,000 nanometers.

12. A personal care composition comprising particles formed from the method of claim 1, wherein the particles have a dynamic viscosity of at least 100 million centipoise measured at a temperature of 25° C. and at $10^{-1}$ Hertz.

13. A film comprising the particles formed from the method of claim 1, wherein the particles have a dynamic viscosity of at least 100 million centipoise measured at a temperature of 25° C. and at $10^{-1}$ Hertz.

14. A method of forming particles having an average diameter of at least 30 nanometers, said method comprising the step of forming an oil-in-water emulsion comprising a silanol, a cyclic silazane, an isocyanate and less than 0.1 weight percent of a hydrophobic costabilizer such that the silanol, the cyclic silazane, and the isocyanate react to form the particles having the average diameter of at least 30 nanometers.

15. The method of claim 14 wherein the step of forming the oil-in-water emulsion is further defined as forming a water-in-oil emulsion comprising the silanol, the cyclic silazane, the isocyanate, and less than 0.1 weight percent of a hydrophobic costabilizer and phase inverting the water-in-oil emulsion to form the oil-in-water emulsion; or applying shear to the water-in-oil emulsion to form the oil-in-water emulsion.

16. The method of claim 15 wherein the oil-in-water emulsion is free of the hydrophobic costabilizer, the silanol has the chemical formula $H(OSiR^1R^2)_nOH$ wherein each of $R^1$ and $R^2$ is independently selected from the group of alkyl groups, cyclic alkyl groups, and combinations thereof, and n is a number from 700 to 900, the cyclic silazane is further defined as 1,1,2,4-tetramethyl-1-sila-2-azacyclopentane, the isocyanate is further defined as hexamethylene diisocyanate, and the particles have an average diameter of greater than 500 nanometers and up to 1,000 nanometers.

17. An oil-in-water emulsion comprising:
  A. particles having an average diameter of at least 30 nanometers and comprising a polymerization product of a silanol, a cyclic silazane, and an isocyanate polymerized in the oil-in-water emulsion; and
  B. less than 0.1 weight percent of a hydrophobic costabilizer, wherein said particles have a dynamic viscosity of at least 100 million centipoise measured at a temperature of 25° C. and at $10^{-1}$ Hertz.

18. The oil-in-water emulsion of claim 17 wherein said silanol has the chemical formula $H(OSiR^1R^2)_nOH$ wherein each of $R^1$ and $R^2$ is independently selected from the group of alkyl groups, cyclic alkyl groups, and combinations thereof and n is a number of from 1 to 2,000.

19. The oil-in-water emulsion of claim 18 wherein said cyclic silazane is further defined as 1,1,2,4-tetramethyl-1-sila-2-azacyclopentane, n is a number of from 700 to 900, the isocyanate is further defined as hexamethylene diisocyanate, and the particles have a diameter of greater than 500 nanometers and up to 1,000 nanometers.

\* \* \* \* \*